US00PP32462P2

(12) United States Plant Patent
Molnar et al.

(10) Patent No.: US PP32,462 P2
(45) Date of Patent: Nov. 17, 2020

(54) ***CORYLUS* PLANT NAMED 'MONMOUTH'**

(50) Latin Name: ***Corylus avellana* cultivar**
Varietal Denomination: Monmouth

(71) Applicant: RUTGERS, THE STATE UNIVERSITY OF NEW JERSEY, New Brunswick, NJ (US)

(72) Inventors: Thomas J. Molnar, East Brunswick, NJ (US); Shawn A. Mehlenbacher, Corvallis, OR (US); John M. Capik, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/602,127

(22) Filed: Aug. 12, 2019

(51) Int. Cl.
*A01H 5/08* (2018.01)
*A01H 6/00* (2018.01)

(52) U.S. Cl.
USPC ..... Plt./152
CPC ..... *A01H 6/00* (2018.05)

(58) Field of Classification Search
USPC ..... Plt./152
CPC ..... A01H 5/0825
See application file for complete search history.

(56) References Cited

PUBLICATIONS http://thescalepit.com/ContentHN/Hazel%20Dormancy%20and%20Pollination.pdf; Apr. 8, 2019; 9 pages.*

* cited by examiner

*Primary Examiner* — Kent L Bell
(74) *Attorney, Agent, or Firm* — Patrick J. Daugherty; Daugherty & Del Zoppo Co., LPA

(57) ABSTRACT

A new and distinct *Corylus avellana* plant named 'Monmouth' characterized by a vigorous and upright growth habit, the production of nuts with globular kernels that fall free of the husk at maturity, and a high level of tolerance (quantitative resistance) to eastern filbert blight caused by the fungus *Anisogramma anomala* (Peck) E. Müller.

5 Drawing Sheets

Latin name: *Corylus avellana* cultivar.
Variety denomination: 'Monmouth'.

BACKGROUND OF THE INVENTION

The present invention relates to a new and distinct cultivar of *Corylus* plant, botanically known as *Corylus avellana* and the designation 'Monmouth', or as 'Monmouth' Hazelnut (H3FR05P69 Rutgers 3), and hereinafter referred to by the name 'Monmouth'. The new *Corylus* resulted from a controlled cross of the female parent 'Sacajawea' (unpatented, Mehlenbacher et al., 2008) with pollen of OSU 616.055 (unpatented) made in 2004. Hybrid seeds resulting from the cross were harvested in August 2004. They were provided a period of moist chilling, subsequently germinated, and the seedlings were grown in the greenhouse during the summer of 2005. From this cross, a total of 106 seedling trees were planted in a controlled research field in East Brunswick, N.J., in October 2005. 'Monmouth' was discovered and selected as a single plant within that progeny of the stated cross-pollination. It was originally assigned the designation H3FR05P69, which indicates the field, row, and tree location of the original seedling.

The female parent 'Sacajawea' was developed at Corvallis, Oreg. and is characterized by excellent kernel quality and tolerance to eastern filbert blight (EFB) caused by the fungus *Anisogramma anomala* (Peck) E. Müller. The male parent OSU 616.055 is an unreleased seedling that also exhibits tolerance to EFB.

'Monmouth' was asexually reproduced by rooted suckers and whip grafting in 2010 through 2015 in East Brunswick and New Brunswick, N.J. The unique features of this new *Corylus* are stable and reproduced true-to-type in successive generations of asexual reproduction.

BRIEF SUMMARY OF THE INVENTION

The following traits have been observed and are determined to be the unique characteristics of 'Monmouth'. These characteristics in combination distinguish 'Monmouth' as a distinct cultivar:

Vigorous and upright-spreading plant habit.

Yellowish-green to green color of developing and fully expanded leaves during the spring and summer.

High level of tolerance (quantitative resistance/horizontal resistance) to eastern filbert blight (EFB) caused by the fungus *Anisogramma anomala* (Peck) E. Müller. The source of this resistance differs from the single dominant allele conferred from 'Gasaway' (unpatented, Mehlenbacher et al., 1991), which protects *Corylus avellana* 'McDonald' (U.S. Pat. No. 28,200 P3, Mehlenbacher et al., 2016), 'Wepster' (U.S. Pat. No. 27,141 P3, Mehlenbacher et al., 2014), 'Dorris' (U.S. Pat. No. 25,022 P3, Mehlenbacher et al., 2013), 'Jefferson' (unpatented, Mehlenbacher et al., 2011a), 'Yamhill' (unpatented, Mehlenbacher et al., 2009), and several other *Corylus avellana* cultivars and pollenizers known to Inventors.

Expression of incompatibility alleles S1 and S12 in the styles.

Comparisons in several replicated plantings in East Brunswick, N.J., show that plants of 'Monmouth' differed from plants of the *Corylus avellana* cultivar 'Barcelona' (unpatented), 'Tonda di Giffoni' (unpatented), 'Yamhill', 'Jefferson', and other cultivars and selections of *Corylus avellana* known to the Inventors, primarily in their response to EFB present in New Jersey, a region where the pathogen is native and highly genetically diverse (Muehlbauer et al., 2019). They also differed in S-alleles, nut size, kernel percentage (ratio of kernel weight to nut weight), frequency of defects (blank nuts, moldy kernels, twin kernels, etc.), time of pollen shed, and length of the husk or involucre.

'Monmouth' is immediately distinguished from its parents and from sibling cultivar 'Hunterdon' (U.S. Plant patent application Ser. No. 16/602,129) by its incompatibility allele (S-allele) combination. 'Monmouth' expresses S-alleles S1 and S12 in its stigmas whereas 'Sacajawea' expresses S1 and S22 and OSU 616.055 expresses S3 and S12, and 'Hunterdon' expresses S1 and S3. 'Monmouth' also differs in its response to the disease eastern filbert blight (EFB) caused by *Anisogramma anomala*. Both 'Sacajawea' and OSU 616.055 express a similar moderate level of tolerance to EFB. For example, previous studies showed 'Sacajawea' exposed to EFB resulted in an average proportion of diseased wood of 21.0% (total length of EFB-diseased stems per tree divided by total length of shoot growth) (see [0142] Capik, J. M. and T. J. Molnar. 2012. Assessment of host (*Corylus* sp.) resistance to eastern filbert blight in New Jersey. J. Amer. Soc. Hort. Sci. 137:157-172). 'Monmouth' has been shown to be highly tolerant expressing an average of only 1.8% diseased wood, and 'Hunterdon' has been shown to be highly tolerant expressing an average of only 2.2% diseased wood.

For example:

Eastern filbert blight response in New Jersey: In a multi-year trial in East Brunswick, N.J., the proportion of EFB-diseased wood across the canopy for 'Monmouth' was 1.8% compared to 20.4% for 'Yamhill', 31.2% for 'Jefferson', 48.6% for 'Gasaway', and 67.0% for 'Barcelona'.

Pollen shed: 'Monmouth' sheds pollen in East Brunswick, N.J., with 'Yamhill' and 'Santiam' (unpatented, Mehlenbacher et al., 2007), after 'Ratoli' (unpatented, minor cultivar from Tarragona, Spain), and prior to 'Jefferson' and 'Gasaway'. 'Monmouth' descriptor=5.

Husk Length: 'Monmouth' is 1.5 times nut length, like 'Barcelona', while 'Wepster' is 2.0 times nut length.

'Monmouth' produces kernels that are well-suited for the blanched kernel market for use in confections and baked goods. 'Monmouth' combines very high levels of tolerance to eastern filbert blight (evaluated against *Anisogramma anomala* strains present in New Jersey, US) with globular nuts and kernels, high kernel percentage, and very good kernel blanching. The tree is vigorous with an upright branching habit that produces a desirable orchard tree when pruned to a single stem.

Field observations in East Brunswick, N.J., and results from greenhouse-based inoculations performed in New Brunswick, N.J., indicate that 'Monmouth' expresses a very high level of tolerance to eastern filbert blight (EFB) caused by the fungus *Anisogramma anomala*. While the cultivar is not immune to EFB, it rarely produces stem cankers and most that develop are small in size and lack fully formed reproductive stromata which show limited sporulation, equating to very little to no stem dieback and a greatly reduced canopy inoculum load even when infections are present. The high level of tolerance (horizontal resistance) is conferred by both of its unrelated, EFB-tolerant parent trees, which is unlike the cultivars currently grown in Oregon and Washington protected by the single dominant 'Gasaway' resistance allele. EFB is now present throughout the Willamette Valley of Oregon where 99% of the U.S. hazelnut crop is grown and is endemic to the eastern US and southern Canada, where it has been historically impossible to grow *Corylus avellana* commercially. 'Monmouth' was selected in central New Jersey and is adapted to the climate present in this region. Pruning to remove cankers and fungicide applications are currently used to manage the disease in orchards of 'Barcelona' and other susceptible cultivars in the Pacific Northwestern US. 'Monmouth' is suitable for planting in areas with high EFB disease pressure. It has shown excellent tolerance in the eastern US where the EFB fungus is native and genetically diverse (Muehlbauer et al., 2019).

BRIEF DESCRIPTION OF THE DRAWINGS

The figures include color photographic illustrations that illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

DETAILED BOTANICAL DESCRIPTION

Figure 1:
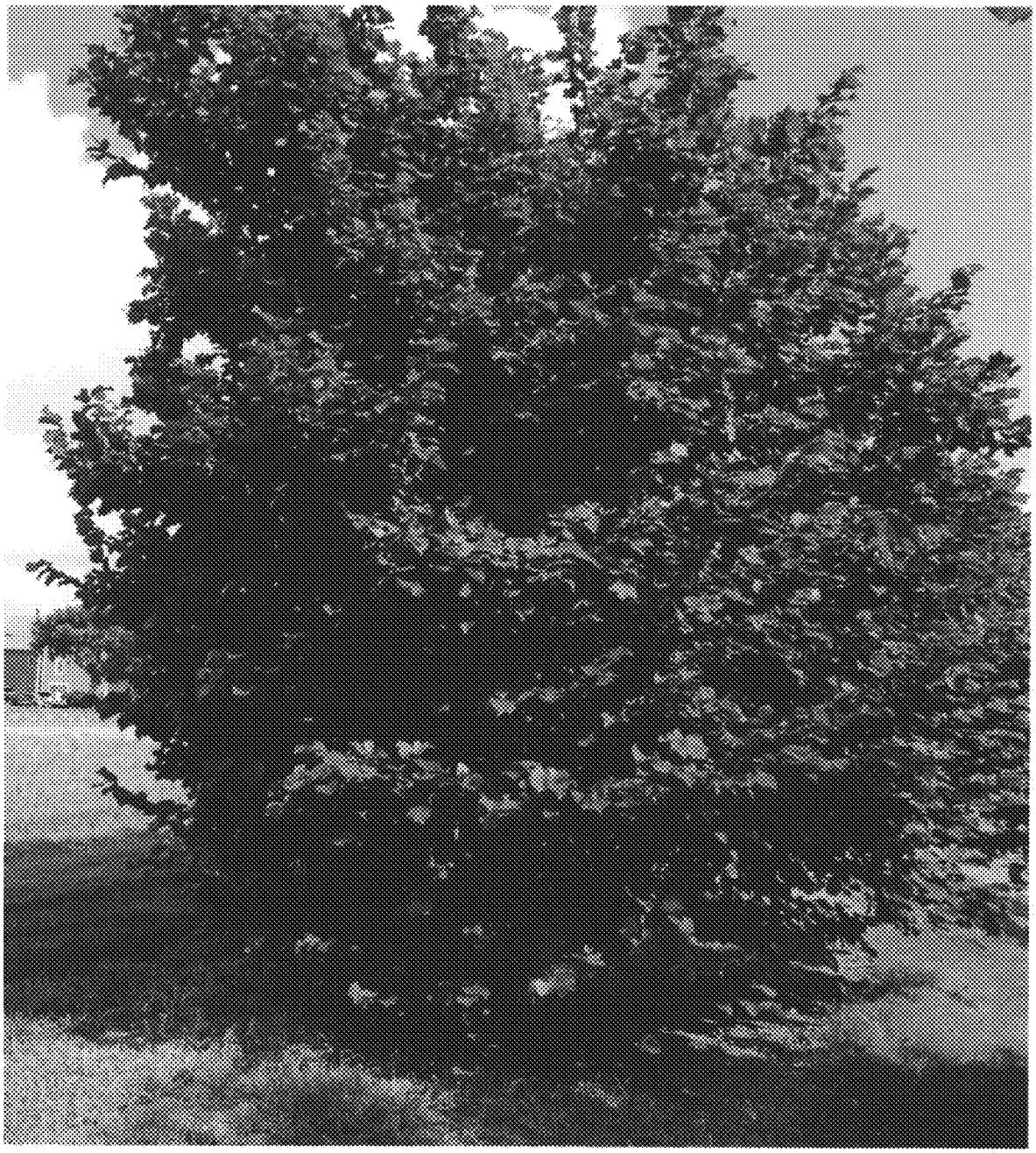
FIG. 1 is a color photographic illustration of an unpruned original tree of the new cultivar 'Monmouth' hazelnut in the 15th leaf.

The cultivar 'Monmouth' has not been observed under all possible environmental conditions. The phenotype may vary somewhat with variations in environment such as temperature and light intensity, without, however, any variance in genotype.

The aforementioned photographs and following observations and measurements describe plants grown in East Brunswick, N.J., under commercial practice outdoors in the field during the spring and summer. Plants used for the photographs and description were the original tree (15 years old) and those propagated by tie-off layerage and growing on their own roots (six and seven years old).

Color references herein are made to The Royal Horticultural Society Colour Chart, 1966 Edition, except where general terms of ordinary dictionary significance are used. International Union for the Protection of New Varieties of Plants ("UPOV") descriptors are described in the Mar. 28, 1979, UPOV Hazelnut guidelines.

Botanical classification: *Corylus avellana* cultivar 'Monmouth'.

Parentage: Female, or seed, parent is *Corylus avellana* 'Sacajawea'. 'Sacajawea' is the result of a cross of OSU 43.091 (unpatented) x 'Sant Pere' (unpatented). 'Sant Pere' is a minor cultivar from Tarragona (Spain) with very early nut maturity (Tasias-Valls, 1975). OSU 43.091 is reported to be the result of self-pollination of 'Montebello' (unpatented, Italian origin), or pollination by an unknown cultivar. 'Sacajawea' has been reported to express a high level of tolerance to EFB in Oregon (Mehlenbacher et al., 2008) and a moderate level in New Jersey (Capik and Molnar, 2012). Male, or pollen, parent is *Corylus avellana* is OSU 616.055 (unpatented, unreleased seeding). OSU 616.055 is the result of a cross of OSU 309.074 x OSU 280.036. OSU 309.074 (unpatented) is the result of a cross of 'Tonda Gentile delle Langhe' (unpatented, Italian origin) x OSU 23.017 (unpatented), which is the result of a cross of 'Barcelona' x 'Extra Ghiaghli'. OSU 280.036 (unpatented) is a cross of 'Tonda di Giffoni' (unpatented) x 'Willamette' (unpatented, Mehlenbacher et al., 1991), both of which are tolerant to EFB.

*Incompatibility alleles*.—'Monmouth' has the incompatibility alleles S1 and S12. Female parent 'Sacajawea' has the alleles S1 and S22 and its male parent OSU 616.055 has the alleles S3 and S12. 'Tonda di Giffoni' has the alleles S2 and S23, 'Tonda Pacific' (U.S. Pat. No. 22,715, Mehlenbacher et al., 2011b) and 'Wepster' have the alleles S1 and S2, and 'McDonald' has the alleles S2 and S15.

Propagation (type rooted suckers):

*Time to initiate roots*.—About 30 days at 20° C.

*Time to produce a rooted young plant*.—About six months at 22° C.

*Root description*.—Fine to thick; freely branching; creamy white in color.

Propagation (type whip grafting):

*Time to budbreak on the scions*.—About 14 days at 25° C.

*Time to produce a grafted plant*.—About six months at 25° C.

Plant description:

*General appearance*.—Natural habit is perennial shrub, but in commercial orchards, is a single trunk tree; rounded, spreading plant habit.

*Growth and branching habit*.—Freely branching; about 15 lateral branches develop per plant; pinching, that is, removal of the terminal apices, enhances branching with lateral branches potentially forming at every node.

*Vigor*.—Vigorous growth habit.

*Size*.—Plant height is about 4.6 meters; plant diameter or spread is about 5.2 meters.

*Trunk at* 30 *cm above the soil line*.—8.5 cm in 2019. Texture is mostly smooth, glabrous.

*Trunk color*.—197C.

Lateral branch description:

*Length*.—About 30.7 cm; ranges from 22 .0 cm to 40.0 cm.

*Diameter*.—About 6.2 mm; ranges from 5.0 mm to 7.0 mm.

*Internode length* (*at base*).—About 0.8 cm.

*Internode length* (*at tip*).—About 4.0 cm; ranges from 2.0 cm to 5.4 cm.

*Texture*.—Smooth, pubescent.

*Strength*.—Strong.

*Color, immature*.—146D.

*Color, mature*.—152B.

*Color of previous seasons branches*.—199B.

Foliage description:

*Arrangement*.—Alternate, simple.

*Length*.—About 13.5 cm; ranges from 11.8 cm to 14.6 cm.

*Width*.—About 10.4 cm; ranges from 8.9 cm to 11.5 cm.

*Shape*.—Oblong to ovate.

*Apex*.—Obtuse to acute.

*Base*.—Cordate.

*Margin*.—Serrate.

*Texture, upper and lower surfaces*.—Slightly pubescent.

*Venation pattern*.—Pinnate.

*Color, developing foliage*.—Upper surface 144B, lower surfaces, 144C.

*Color, fully expanded foliage, upper surface*.—Spring and summer, 137A; late summer and fall, 137A.

*Color, fully expanded foliage, lower surface*.—Spring and summer, 137D; late summer and fall, 137D.

*Color venation, upper surface*.—Spring and summer, 145B; late summer and fall, 145B.

*Color venation, lower surface*.—Spring and summer, 145B; late summer and fall, 145B.

Leaf bud description:

*Shape*.—Globular. Length: average 8.0 mm. Diameter: average 6.0 mm

*Time of leaf budbreak*.—Medium to late, Descriptor-6; H3FR05P69 budbreak is approximately one week before Jefferson, about five days after Yamhill, and one day later than Santiam.

*Color*.—145B.

Petiole description:

*Length*.—About 1.5 cm; ranges from 1.0 cm to 2.0 cm.

*Diameter*.—About 1.7 mm; ranges from 1.5 mm to 2.0 mm.

*Texture, upper and lower surfaces*.—Pubescent.

*Color*.—144B.

Flower description:

*Male inflorescences*.—Catkins.

*Color prior to elongation*.—176D.

*Catkin length*.—Average 30.0 mm. Catkin diameter: average 6.5 mm

*Female inflorescence style color*.—47B. Female inflorescence length at full maturity: average 7.0 mm

*Time of female flowering*.—Early to medium, Descriptor-4.

*Time of female flowering compared to male flowering*.—Protogyny, Descriptor-1. Time of male flowering: Very early, Descriptor-2.

*Involucre constriction*.—Absent.

*Involucre length*.—1.5 times length of nut, Descriptor-7.

*Size of indentation*.—Medium, Descriptor-5.

*Strength of serration of indentation*.—Strong, Descriptor-7.

*Thickness of callus at base*.—Medium, Descriptor-5.

*Pubescence on husk*.—Absent, Descriptor-1.

*Density of hairiness of involucre*.—Weak, Descriptor-3.

*Jointing of bracts*.—One on side, Descriptor-3.

Nut description:

*Length*.—Average 19.2 mm.

*Width*.—Average 19.3 mm.

*Depth*.—Average 17.2 mm.

*Nut shape*.—Globular, Descriptor-2.

*Nut shape index*.—(Width+Depth)/2*Length=0.95.

*Nut compression index*.—(Width/Depth)=1.12.
*Nut weight*.—Average 2.46 g.
*Kernel weight*.—Average 1.25 g.
*Kernel percentage* (kernel weight/nut weight).—Average 50.7%.
*Number of fruits per cluster*.—Two to three.
*Nutshell coloration*.—164A.
*Number of stripes on shell*.—Medium, Descriptor-5.
*Shape of fruit apex*.—Obtuse, Descriptor-2.
*Prominence of fruit apex*.—Medium prominence, Descriptor-3.
*Size of fruit pistil scar on shell*.—Very small, Descriptor-3.
*Hairiness of top of fruit*.—Medium, Descriptor-5.
*Curvature of nut basal scar*.—Flat, Descriptor-2.
*Double kernels*.—Absent.
*Kernel shape*.—Globular, Descriptor-2.
*Shape of kernel in cross-section*.—Circular, Descriptor-2.
*Lateral groove in kernel*.—Present.
*Corkiness of pellicle of kernel*.—Smooth, Descriptor-1.
*Disease/pest resistance*.—Plants of 'Monmouth' exhibit a very high level of tolerance to EFB, referred to as quantitative resistance or horizontal resistance, caused by the fungus *Anisogramma anomala* (Peck) E. Müller. It has been evaluated against the strains of the fungus present in New Jersey (Muehlbauer et al., 2019); a few small cankers may develop under high disease pressure but they typically lack stromata equating to reduce sporulation and subsequent orchard inoculum load. Plants have not been challenged against all strains of *Anisogramma anomala* present in North America and have not been thoroughly evaluated for their tolerance of bud mites (*Phytoptus avellanae* Nal.); no bud mites were observed on the original tree or its propagules grown in East Brunswick, N.J. Further, no bacterial blight caused by *Xanthomonas campestris* pv. *corylina* was observed on the cultivar during the course of evaluations.
*Temperature tolerance*.—'Monmouth' was selected in East Brunswick, N.J., and is targeted for production in USDA Plant Hardiness Zone 6a to 7b. Plants of the new *Corylus avellana* have been observed to tolerate temperatures from −21 to 38° C.

COMPARATIVE DATA

Figure 4:
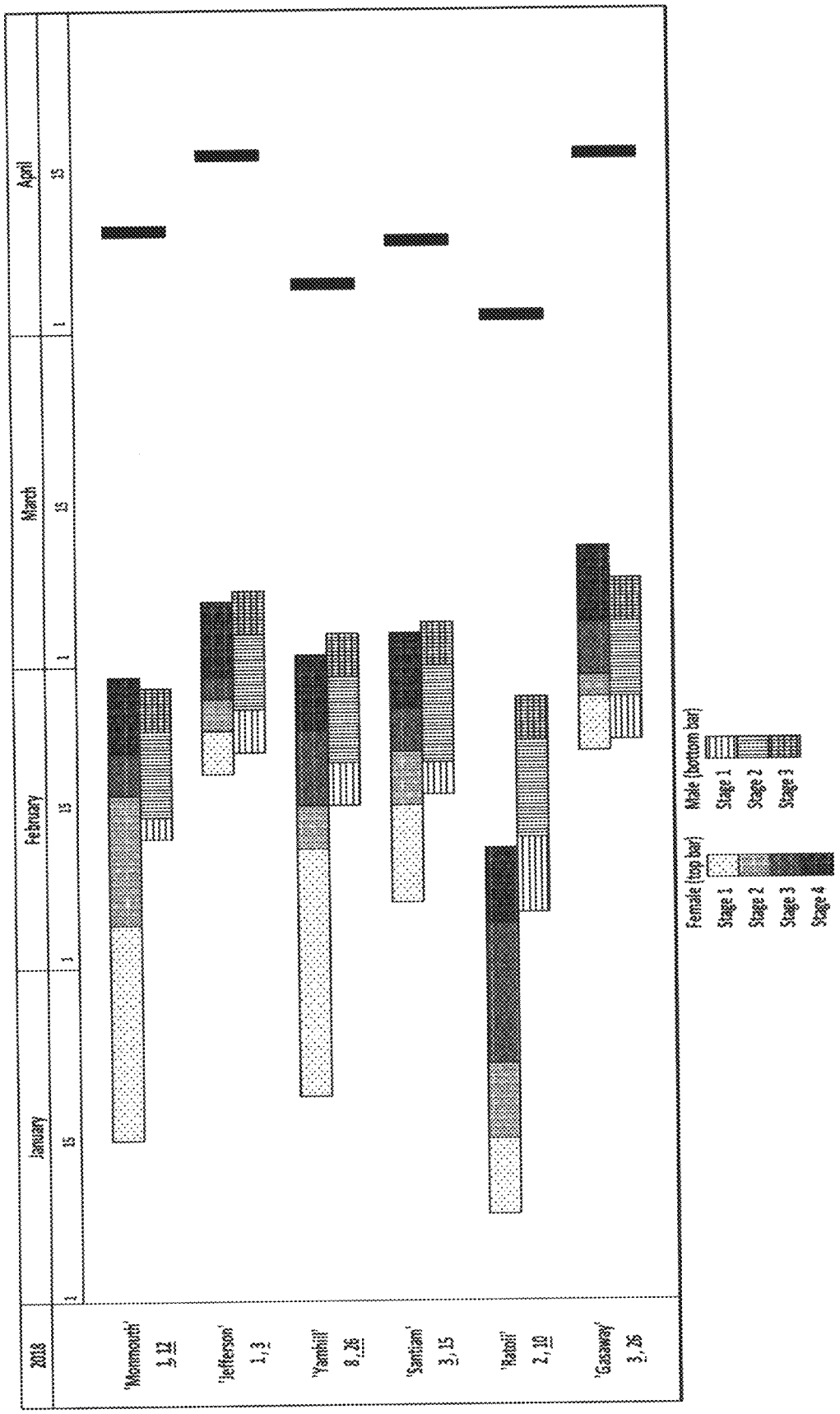
FIG. 4 is a phenology chart illustration that shows times of female receptivity, pollen shed, and vegetative budbreak of 'Monmouth' and other hazelnut cultivars.

FIG. 4 presents a phenology chart showing time of female receptivity, pollen shed, and vegetative budbreak of 'Monmouth' and other hazelnut cultivars grown in East Brunswick, N.J. over a time period from January to April of 2018. For each of the different indicated varieties ('Monmouth', 'Jefferson', 'Yamhill', 'Santiam', 'Ratoli' and 'Gasaway') upper and lower bar graph pairings are provided in alignment with their respective varietal indicators, wherein the upper (top) bar graph of each pairing represents pistillate (female) flower development as it progresses over time through each of four stages represented by the crosshatchings key at the bottom of the chart; and the lower (bottom) bar graph of each pairing represents staminate (male) flower development as it progresses over time through each of three stages represented by different crosshatchings defined by another key at the bottom of the chart. The different respective stages correspond to the stages of development as defined and described in "Flowering phenology of eastern filbert blight-resistant accessions in New Jersey," Capik, J. M. and T. J. Molnar, HortTechnology 24:196-208, 2014 (hereinafter sometimes "Capik and Molnar (2014)"). Stage 1 of vegetative bud development for each of the varieties is represented by the solid black rectangles aligned with the varietal indicators.

Figure 5:
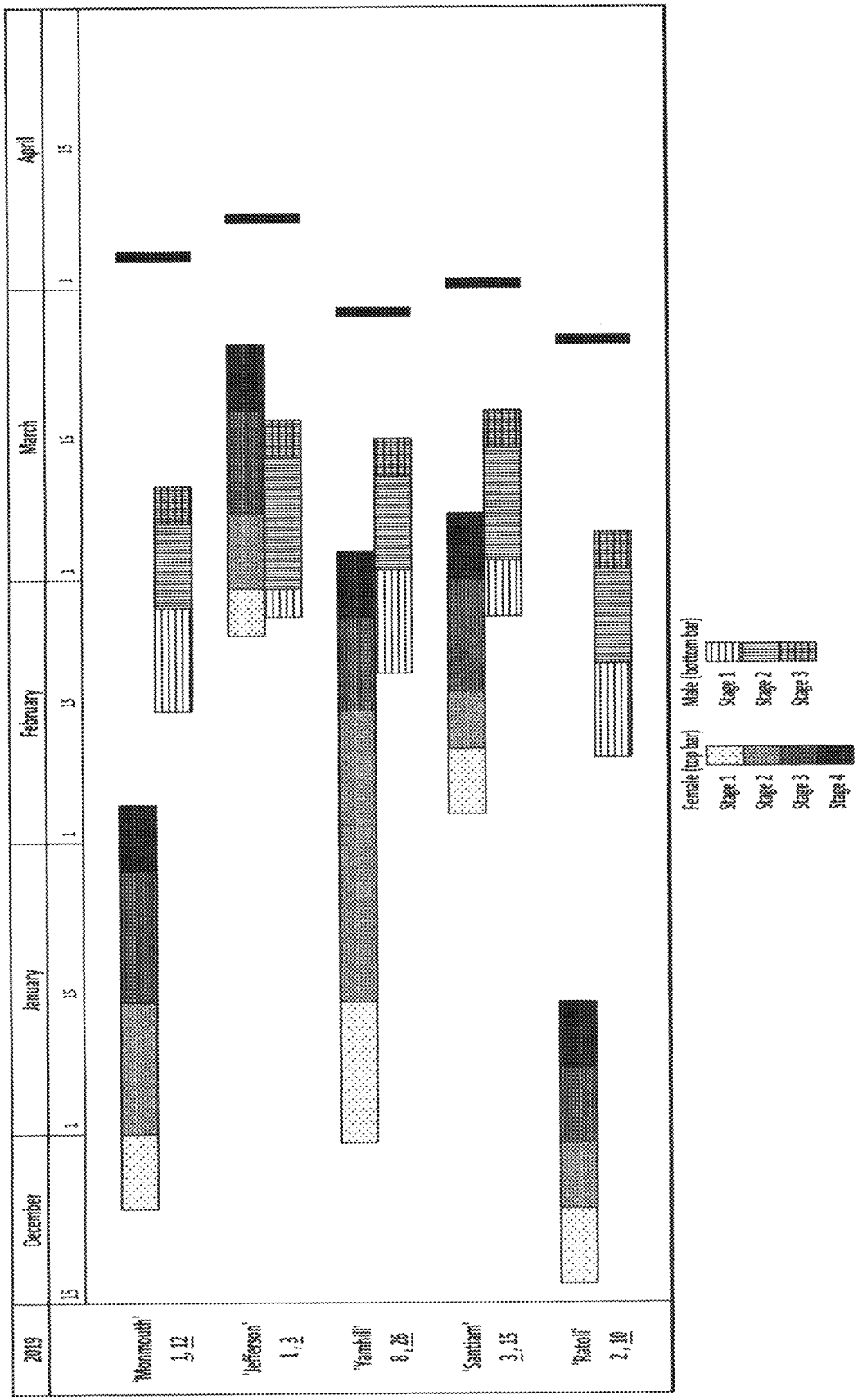
FIG. 5 is a phenology chart illustration that shows times of female receptivity, pollen shed, and vegetative budbreak of 'Monmouth' and other hazelnut cultivars.

FIG. 5 presents a phenology chart showing time of female receptivity, pollen shed, and vegetative budbreak of 'Monmouth' and other hazelnut cultivars grown in East Brunswick, N.J., from December 2018 to April 2019. For each of the different indicated varieties ('Monmouth', 'Jefferson', 'Yamhill', 'Santiam', and 'Ratoli') upper and lower bar graph pairings are provided in alignment with their respective varietal indicators, wherein the upper (top) bar graph of each pairing represents pistillate (female) flower development as it progresses over time through each of the four Capik and Molnar (2014) stages represented by the crosshatchings key at the bottom of the chart; and the lower (bottom) bar graph of each pairing represents staminate (male) flower development as it progresses over time through each of three Capik and Molnar (2014) stages represented by crosshatchings defined by another key at the bottom of the chart. Stage 1 of vegetative bud development for each of the varieties is represented by the solid black rectangles aligned with the varietal indicators.

*Disease resistance*.—'Monmouth' differs from existing *Corylus avellana* cultivars based on its source and type of resistance to eastern filbert blight (EFB) caused by *Anisogramma anomala*. Commercial cultivars previously widely grown in Oregon including 'Barcelona' (unpatented), 'Ennis' (unpatented), 'Daviana' (unpatented), 'Butler' (unpatented), etc. are highly susceptible to EFB and cannot be grown in the eastern US without copious applications of chemical fungicides and heavy pruning. Tree death can occur in the eastern US within 5 years of exposure to the systemic fungus. The more recently developed cultivars 'Santiam', 'Yamhill', 'Jefferson', 'Dorris', 'Wepster', and 'McDonald' and their associated pollenizers are protected from EFB by a single resistance gene conferred from *Corylus avellana* 'Gasaway'. This gene provides a high level of resistance in Oregon and Washington where the diversity of the fungus is limited (Muehlbauer et al., 2019), but does not provide a similar level of protection from disease in the eastern US where the pathogen is endemic and genetically diverse (Capik and Molnar, 2012; Muehlbauer et al., 2018). 'Monmouth' hazelnut is highly tolerant to EFB but does not carry the single 'Gasaway' resistance allele. It was developed by crossing two unrelated *Corylus avellana* plants both exhibiting a high level of tolerance and then selecting offspring exhibiting enhanced levels of tolerance in the presence of high disease pressure in East Brunswick, N.J. While 'Monmouth' plants are not immune to EFB, they have been shown to rarely get destructive stem cankers that lead to stem die-back and yield decline. In a multi-year trial in East Brunswick, N.J., completed in winter 2018 and spanning more than 8 years of exposure to EFB, the average proportion of diseased wood (total length of EFB-diseased stems per tree divided by total length of shoot growth) for 'Monmouth' was 1.8% compared to 20.4% for 'Yamhill' (unpatented, Mehlenbacher et al 2009), 31.2% for 'Jefferson' (unpatented, Mehlenbacher et al. 2011a), and 48.6% for 'Gasaway' (unpatented). Previous studies in New Jersey showed the proportion of diseased wood of 'Barcelona' to be 67.0%, 'Tonda di Giffoni' 39%, and 'Sacajawea' 21% (Capik and Molnar, 2012). Differences were also observed in the number of cankers and average canker length for 'Monmouth' in comparison to 'Yamhill', 'Jefferson', and 'Gasaway' in the study completed in 2018. 'Monmouth' exhibited an average of 6.5 cankers per tree with an average canker length of 26.1 cm. In contrast, 'Gasaway' exhibited an average of 93.0 cankers per tree with an average length of 130.8 cm, 'Jefferson' exhibited an average of 36.9 cankers per tree with an average length of 72.3 cm, and 'Yamhill' exhibited an average of 40.5 cankers per tree with an average length of 37.9 cm. As reported in Capik and Molnar (2012), and as a further point of comparison in regard to EFB response, 'Barcelona' exhibited an average of 20.4 cankers per tree with an average length of 61.9 cm, 'Tonda di Giffoni' exhibited an average of 39.0 cankers per tree with an average length of 24.5 cm, and 'Sacajawea' exhibited an average of 7.7 cankers per tree with an average length of 21.5 cm (Capik and Molnar, 2012). While 'Sacajawea', a cultivar known to exhibit tolerance to EFB, exhibits similar canker numbers per tree and canker length to 'Monmouth', its proportion of diseased wood is much higher at 21%, compared to 1.8%.

Figure 3:
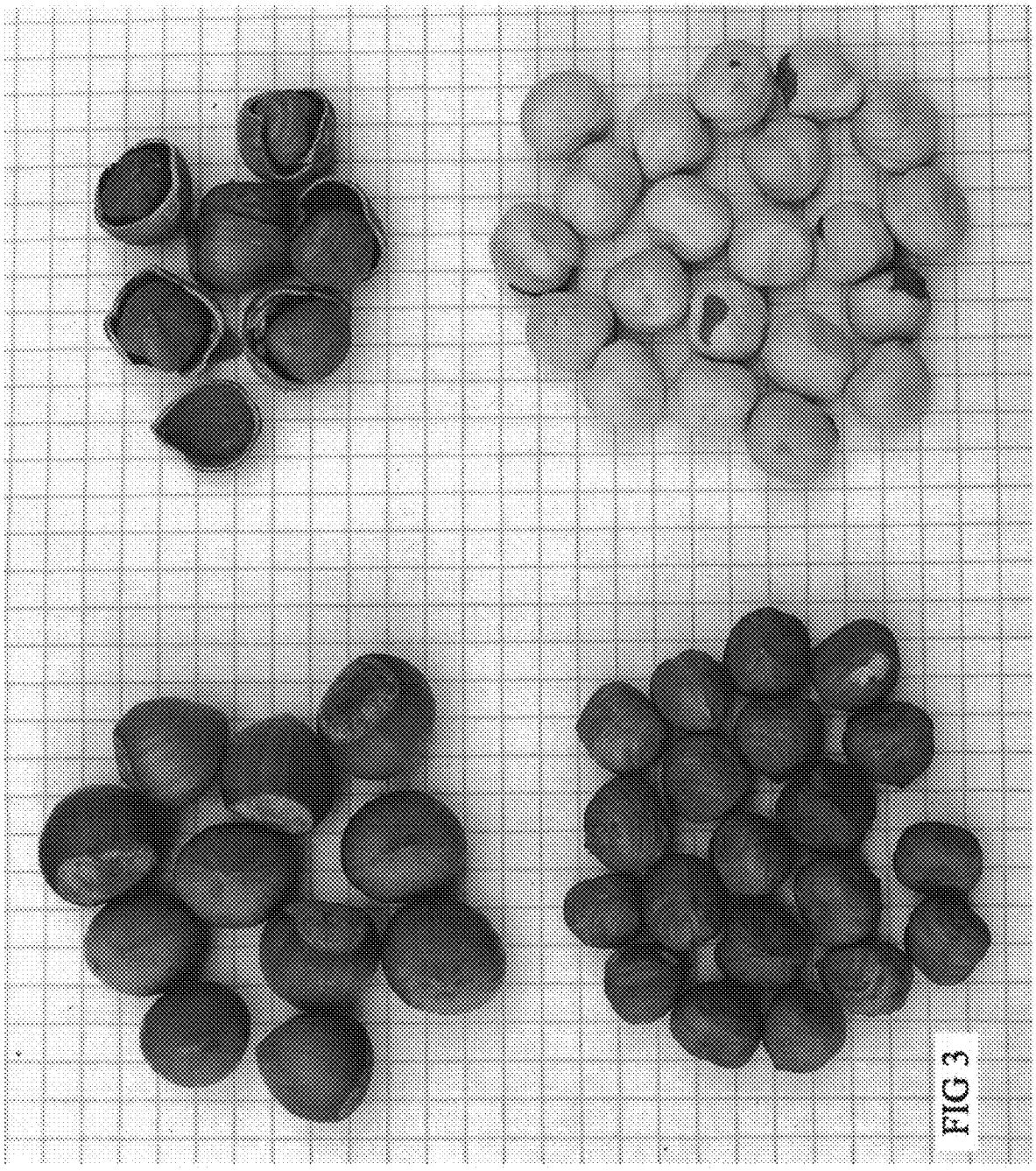
FIG. 3 is a color photographic illustration of nuts, cracked shells, raw kernels, and blanched kernels of hazelnuts of the 'Monmouth'.

*Nut and kernel characteristics*.—'Monmouth' hazelnut is targeted for the blanched kernel market and specifically for nut production in the eastern United States in USDA Plant Hardiness Zone 6a to 7b where most existing cultivars of *Corylus avellana* cannot be grown due to the impacts of EFB. The nut shape is globular with a slight point. Kernels are globular also with a slight point. The average single nut weight over the past 6 years for 'Monmouth' is 2.46 g and average single kernel weight is 1.25 g, with an average kernel to nut ratio of 50.7% (FIG. 3). 'Monmouth' nuts and kernels are smaller than those of 'Barcelona', 'Jefferson', and 'Sacajawea', and also differ in kernel to nut ratio. For example, 'Barcelona' (as described in Mehlenbacher et al., 2008) had an average single nut weight of 3.85 grams, average single kernel weight of 1.66 grams, and an average kernel to nut ratio of 43.1%. 'Sacajawea' (as described in Mehlenbacher et al., 2008) had an average single nut weight of 2.79 grams, an average single kernel weight of 1.45 grams, and an average kernel to nut ratio of 52.1%. 'Jefferson' (as described in Mehlenbacher et al., 2011a) had an average single nut weight of 3.69 grams, an average single kernel weight of 1.66 grams, and an average kernel to nut ratio of 42.9%. 'Monmouth' nuts and kernels are slightly larger than 'Yamhill' and 'Wepster' and similar to 'McDonald', but differ from the three in several aspects including ratio of kernel to nut and pellicle removal after roasting. For example, 'Yamhill' (as described in Mehlenbacher et al., 2009) had an average single nut weight of 2.34 grams, an average single kernel weight of 1.13 grams, and an average kernel to nut ratio of 49.3%. 'Wepster' (as described in Mehlenbacher et al., 2014) had an average single nut weight of 2.39 grams, an average single kernel weight of 1.11 grams, and an average kernel to nut ratio of 46.6%. 'McDonald' (as described in Mehlenbacher et al., 2016) had an average single nut weight of 2.39 grams, an average single kernel weight of 1.21 grams, with an average kernel to nut ratio of 50.7%. Raw kernels of 'Monmouth' have a light brown pellicle with a very small amount of attached fiber (average rating was 1.2 on a scale of 1 [no fiber] to 4 [much fiber] with average based on 4 years of evaluations). Pellicle removal after roasting at 150° C. for 15 min and rubbing is rated on a scale of 1 (complete pellicle removal) to 7 (no pellicle removal). Nearly all of the pellicle on 'Monmouth' kernels is removed after roasting with an average rating of 1.3 (averaged from 4 years of evaluations). 'Monmouth' demonstrated better average pellicle removal than that reported in Oregon for 'Barcelona' (4.2 out of 7.0 as described in Mehlenbacher et al., 2008), 'Jefferson' (3.9 out of 7.0 as described in Mehlenbacher et al., 2011a), 'Yamhill' (4.1 out of 7.0 as described in Mehlenbacher et al., 2011a), and 'McDonald' (3.8 out of 7.0 as described in Mehlenbacher et al., 2016), 'Sacajawea' (2.9 out of 7.0 as described in Mehlenbacher et al., 2011), and 'Dorris' (2.4 out of 7.0 as described in Mehlenbacher et al., 2013). It is similar to 'Tonda Pacifica' as described in Mehlenbacher et al. (2011), which is reported to have a score of 1.5 out of 7. The average percentage of good kernels (kernels free of defects) was calculated for 'Monmouth' and found to be 82.0%. There was no occurrence of moldy kernels; however, there was on average 6.0% blank nuts, 9.5% nuts with shriveled kernels, 0.5% poorly filled, and 2.0% defective kernels attributed to defects from sucking insect damage, primarily Brown Marmorated Stink Bug (*Halyomorpha halys*, Stål, 1855). The percentage of good kernels for 'Monmouth' was considerably higher than that reported for 'Barcelona' in multiple reports from Oregon (60.9% good kernels reported in Mehlenbacher et al. [2008] and 69.4% in Mehlenbacher et al. [2013]). The average percentage of good kernels for 'Monmouth' grown in New Jersey is slightly lower than the range reported in Oregon for 'Yamhill', 'Jefferson', 'Dorris', and 'McDonald'; however, the percentage of moldy nuts was generally higher for these cultivars. There were no instances of doubles or black tips for 'Monmouth'.

Figure 2:
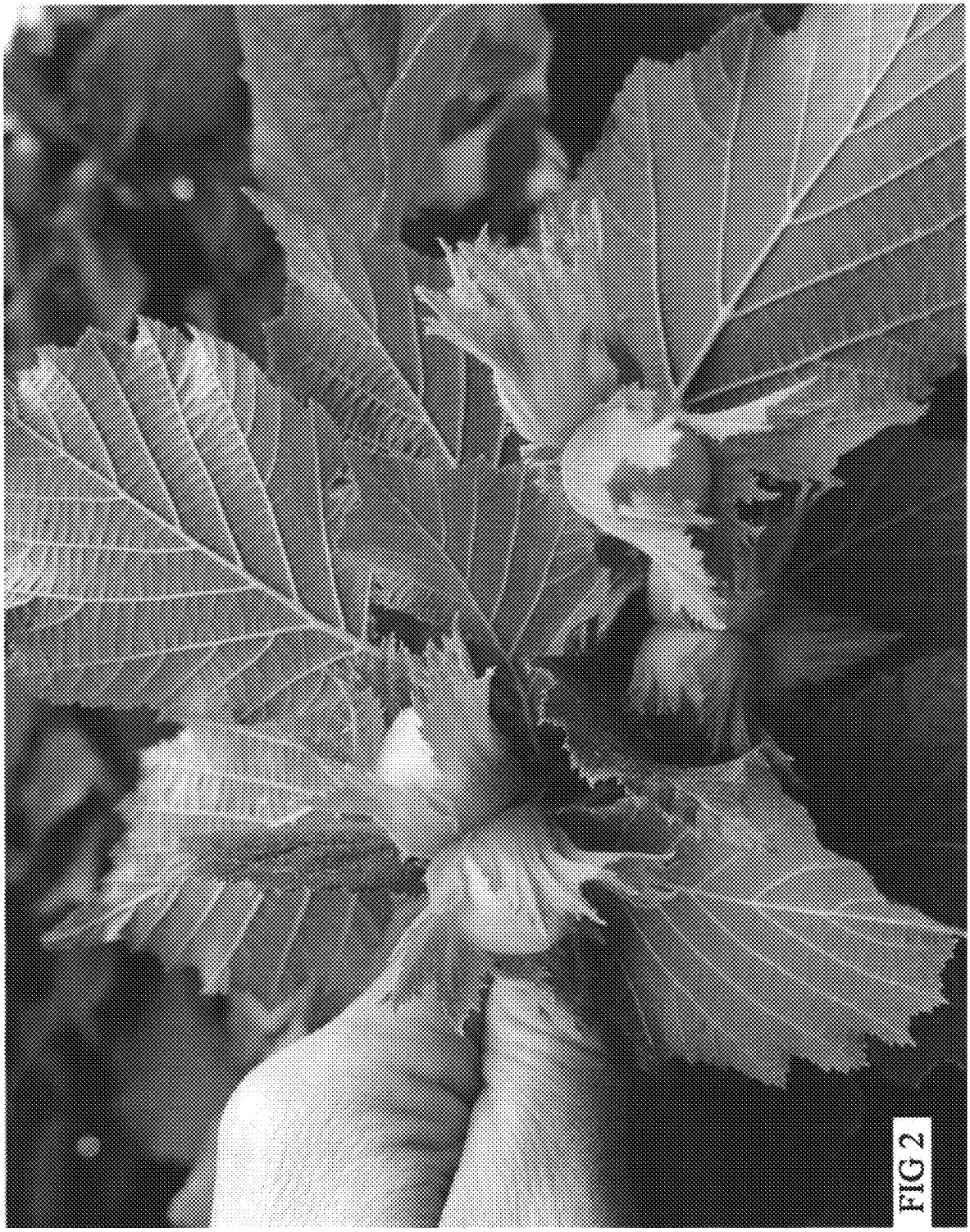
FIG. 2 is a color photographic illustration of nuts, husks and leaves of the 'Monmouth' hazelnut.

*Nut maturity date*.—The nuts of 'Monmouth' are typically borne in clusters of 2-3 in husks about 50% longer than the nuts. The husks are flared and slit down the side (FIG. 2), and open as they dry at maturity. About 90% of the nuts fall free of the husk at maturity (range 80-100%). The other 10% of the nuts come out of the husks as they move through the harvester. When mature, the shells are tan to light brown in color. Harvest date on average is around 10 days before 'Jefferson' when grown in East Brunswick, N.J., typically around the very last days of August or the first week of September.

*Incompatibility and pollinizers*.—The trees set a moderate to high amount of catkins that shed pollen in early mid-season a few days prior to 'Yamhill'.

Pollen has been collected and used in several controlled pollinations, and both quantity and viability appear to be good. 'Monmouth' has incompatibility alleles S1 and S12 as determined by fluorescence microscopy. Both alleles are expressed in the female flowers as well as the pollen because of co-dominance expressed by the S1 and S12 allele. By convention, alleles expressed in the pollen are underlined. Time of pollen shed and female receptivity were recorded weekly from early December 2017 to late March 2019 (FIGS. 4-5). Climatic conditions vary each year and impact dates of bloom but not usually the order of progression of bloom among cultivars. Female inflorescences of 'Monmouth' emerge in early season and are generally fully receptive around the first week of February in New Jersey but may emerge earlier during warm spells. Pollinizer cultivars that shed compatible pollen in midseason and late midseason are recommended, with hybrid hazelnut seedlings (*Corylus americana* x *C. avellana*) planted as pollenizers in eastern and northern regions where cold temperatures and fluctuating climatic conditions can affect pollen production of *C. avellana*. Alternative orchard designs include planting different eastern filbert blight resistant cross-compatible cultivars in adjacent rows to augment pollen production. Flowering times will continue to be observed and pollinizer recommendations adjusted accordingly. Pollinizers must be selected that express a high level of EFB resistance to eliminate/reduce the need for fungicide control in the entire orchard.

*Pests and diseases*.—Based on field trials under high disease pressure and greenhouse inoculation trials, both performed in New Jersey, 'Monmouth' expresses a very high level of tolerance to EFB (quantitative resistance). Fungicide applications to control EFB are not expected to be needed. Small cankers that may develop can be removed through pruning to reduce inoculum load in production orchards. Susceptibility to bacterial blight caused by *Xanthomonas campestris* pv. *corylina* has not been quantified, but the original seedling tree and clonal trees in the replicated trials were not affected. Susceptibility to big bud mite (primarily *Phytoptus avellanae* Nal.) has not been quantified, but the original tree and trees in the replicated trials were not affected.

*Propagation*.—Layers of 'Monmouth' are vigorous and root well, similar to standard cultivars of *Corylus avellana*

REFERENCES

Capik, J. M. and T. J. Molnar. 2012. Assessment of host (*Corylus* sp.) resistance to eastern filbert blight in New Jersey. J. Amer. Soc. Hort. Sci. 137:157-172.

Capik, J. M. and T. J. Molnar. 2014. Flowering phenology of eastern filbert blight-resistant accessions in New Jersey. HortTechnology 24:196-208.

Mehlenbacher, S. A., M. M. Thompson, and H. R. Cameron. 1991a. Occurrence and inheritance of resistance to eastern filbert blight in 'Gasaway' hazelnut. HortScience 26:410-411.

Mehlenbacher, S. A., A. N. Miller, M. M. Thompson, H. B. Lagerstedt, and D. C. Smith. 1991b. 'Willamette' hazelnut. HortScience 26:1341-1342.

Mehlenbacher, S. A., A. N. Azarenko, D. C. Smith, and R. McCluskey. 2001. 'Clark' hazelnut. HortScience 36:995-996.

Mehlenbacher, S. A., A. N. Azarenko, D. C. Smith, and R. McCluskey. 2007. 'Santiam' hazelnut. HortScience 42:715-717.

Mehlenbacher, S. A., D. C. Smith, and R. L. McCluskey. 2008. 'Sacajawea' hazelnut. HortScience 43:255 257.

Mehlenbacher, S. A., D. C. Smith, and R. L. McCluskey. 2009. 'Yamhill' hazelnut. HortScience 44:845-847.

Mehlenbacher, S. A., D. C. Smith, and R. L. McCluskey. 2011a. 'Jefferson' hazelnut. HortScience 46:662-664.

Mehlenbacher, S. A., D. C. Smith, R. L. McCluskey and M. M. Thompson. 2011b. 'Tonda Pacifica' hazelnut. Hort Science 46:505-508.

Mehlenbacher, S. A., D. C. Smith, and R. L. McCluskey. 2013. 'Dorris' hazelnut. HortScience 48:796-799.

Mehlenbacher, S. A., D. C. Smith, and R. L. McCluskey. 2014. 'Wepster' hazelnut. HortScience 49:346-349.

Mehlenbacher, S. A., D. C. Smith, and R. L. McCluskey. 2016. 'McDonald' hazelnut. HortScience 51:757-760.

Muehlbauer, M. F., Tobia J., Honig, J. A., Zhang N., Hillman, B. I., Morey Gold, K., and Molnar, T. J. 2019. Population differentiation within *Anisogramma anomala* in North America.

Phytopathololgy. Published Online: 29 Apr. 2019 https://doi.org/10.1094/PHYTO-06-18-0209-R.

Tasias-Valls, J. 1975. El avellano en la provincial de Tarragona [in Spanish]. Excma. Diputacio´n Provincial de Tarragona, Fundacio´n Servicio Agropecuario Provincial, Tarragona, Spain.

What is claimed is:

1. A new and distinct cultivar of *Corylus* plant named 'Monmouth', as illustrated and described.

* * * * *